United States Patent [19]

White

[11] 4,099,872
[45] Jul. 11, 1978

[54] FLUORESCENCE SPECTROPHOTOMETER

[76] Inventor: John U. White, Contentment Island Rd., Darien, Conn. 06820

[21] Appl. No.: 731,765

[22] Filed: Oct. 12, 1976

Related U.S. Application Data

[63] Continuation-in-part of Ser. No. 639,804, Dec. 11, 1975, Pat. No. 4,022,529.

[51] Int. Cl.² ............................ G01J 3/30; G01J 3/42
[52] U.S. Cl. ................................... 356/85; 250/458; 356/75; 356/88; 356/94; 356/96
[58] Field of Search .................... 356/75, 85, 88, 93, 356/94, 95, 96, 97, 98, 246; 250/458, 459, 461

[56] References Cited

U.S. PATENT DOCUMENTS

| | | | |
|---|---|---|---|
| 3,606,547 | 9/1971 | Iwahashi | 356/95 |
| 3,972,627 | 8/1976 | Rabl et al. | 356/246 |
| 4,022,529 | 5/1977 | White | 356/85 |

Primary Examiner—Vincent P. McGraw
Attorney, Agent, or Firm—Lee C. Robinson, Jr.

[57] ABSTRACT

A fluorescence spectrophotometer in which a monochromatic beam of radiation is directed from an excitation monochromator through a first optical system to a sample being evaluated. Fluorescence from the sample is collected by a second optical system and is directed to an emission monochromator. These optical systems are arranged such that slit images from the respective monochromators lie in a single plane defined by the intersecting axial rays of the excitation and fluorescence beams. In several advantageous arrangements the optical system includes aspherical mirrors arranged to give different magnifications of the images in the horizontal and vertical planes. The intensity of the excitation beam applied to the sample and of the output signal may be further increased by positioning wedge shaped optical elements adjacent the sample.

19 Claims, 9 Drawing Figures

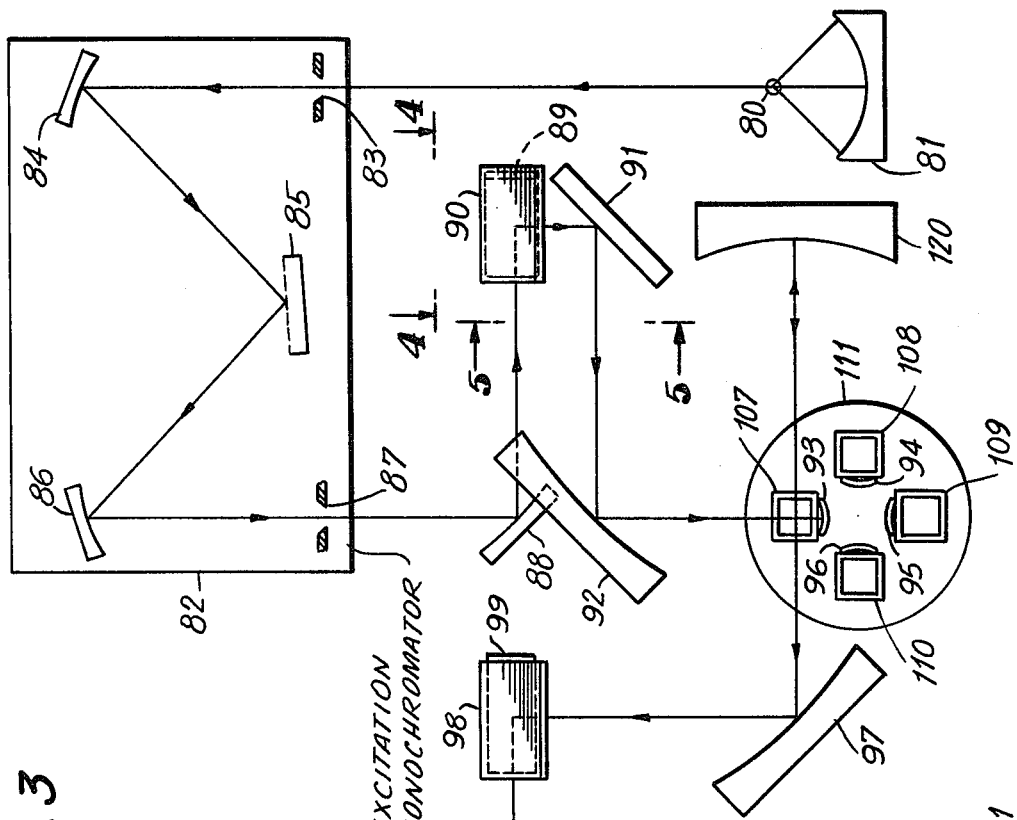
FIG. 3
FIG. 5
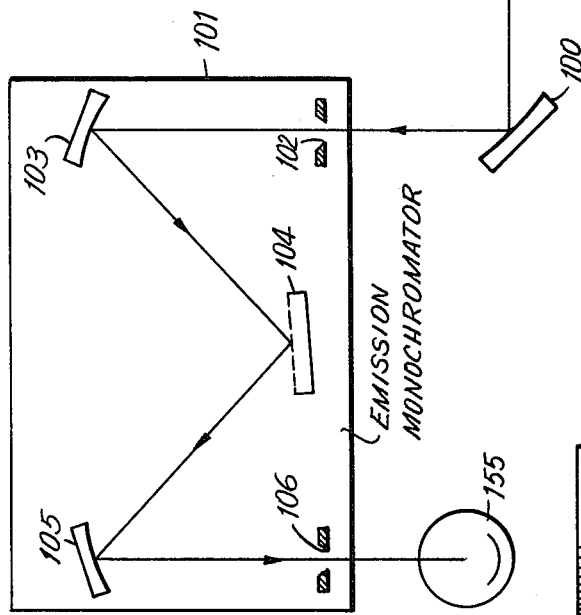
FIG. 4
FIG. 6

FLUORESCENCE SPECTROPHOTOMETER

CROSS-REFERENCE TO COPENDING APPLICATION

This application is a continuation-in-part of U.S. Pat. application Ser. No. 639,804 filed Dec. 11, 1975, now U.S. Pat. No. 4,022,529 granted May 10, 1977 and the disclosure of which is incorporated herein by reference.

BACKGROUND OF THE INVENTION

The present invention relates to radiation measuring apparatus and more particularly to luminescence spectrophotometers of the type in which a sample is irradiated with light of one wavelength and its emission spectrum is observed through the use of a monochromator and a detection system. As used herein and in the appended claims, the term "light" includes not only visible light but also radiation having wavelengths longer and shorter than the visible spectrum.

In the measurement of luminescence, e.g. fluorescence, and excitation spectra it is customary to illuminate a sample with monochromatic light from an intense source and to observe the light emitted by the sample with a monochromator and a photoelectric detection system. Either the excitation or the emission wavelength may be scanned to record the intensity of the spectrum as a function of excitation or emission wavelength.

Heretofore, radiation measuring apparatus of the foregoing type exhibited certain disadvantages. One of the more significant problems was the comparatively low intensity of the output signal particularly in measuring the spectra of dilute materials. In the usual form of apparatus a magnified image of the light source was focused on the entrance slit of the excitation monochromator; and a reduced image of the exit slit was focused on the sample by means of first optical system. Fluorescence from the sample was collected by a second optical system and was focused on the entrance slit of an emission monochromator. The signal at the exit slit of this latter monochromator was proportional to the intensity of the light at the selected wavelength. Attempts to increase the intensity of the signal commonly included a reduction in height of the image of the excitation monochromator's exit slit. These attempts were only partially successful, however, and the measured intensity continued to be insufficient to obtain readings of the desired accuracy for low intensity samples.

SUMMARY

One general object of this invention, therefore, is to provide new and improved apparatus for measuring the intensity of light emitted by a sample with respect to the intensity of the light exciting the sample.

More specifically, it is an object of this invention to provide radiation measuring apparatus which is effective to produce a high intensity fluorescence signal.

Another object of the invention is to provide a fluorescence spectrophotometer utilizing comparatively simple optical components which is economical to manufacture and reliable in operation.

Another object of the invention is to provide an improved optical system in a fluorescence spectrophotometer.

In a presently preferred embodiment of the invention, the apparatus comprises a radiation source and an excitation monochromator for isolating an excitation beam of monochromatic radiation from the source. The excitation monochromator includes limiting apertures which are respectively formed at the excitation entrance slit, at the excitation exit slit and between the slits near the monochromator's dispersing means. The radiation is received by a first optical system and is directed toward the sample being evaluated to cause the sample to emit fluorescence. A second optical system collects fluorescence from the sample and focuses a beam of the collected radiation on the entrance slit of an emission monochromator to produce a monochromatic emission beam at the monochromator's exit slit. In a manner similar to that of the excitation monochromator, the emission monochromator includes limiting apertures at the entrance slit, at the exit slit and between the entrance and exit slits near the dispersing means. The first optical system forms images of the exit and intermediate apertures of the excitation monochromator adjacent two opposite sides of the sample, and the second optical system forms images of the entrance and intermediate apertures of the emission monochromator adjacent two other opposite sides of the sample. The emission beam emerging from the exit slit of the emission monochromator is received by a photoelectric detector to provide an electrical signal proportional to the intensity of the fluorescent light emitted by the sample at the selected wave-length.

In accordance with one feature of several important embodiments of the invention, the longitudinal axes of the images adjacent the sample lie in a single plane defined by the axial rays of the excitation and fluorescence beams. In one embodiment the excitation monochromator exit slit and the emission monochromator entrance slit lie in the same horizontal plane. A beam of light is focused on the entrance slit of the excitation monochromator, and the resulting monochromatic beam from the exit slit passes through an optical system including two concave mirrors which focus the beam on the sample. The arrangement is such that an image of the exit slit aperture is formed adjacent a first surface of the sample, and an image of the intermediate aperture is formed adjacent a second surface of the sample. Similar concave mirrors reflect fluorescence from the illuminated portion of the sample to the emission monochromator. An image of the entrance slit aperture of this latter monochromator is formed adjacent a third surface of the sample, and an image of the intermediate aperture is formed adjacent a fourth surface of the sample. The widths of the slits advantageously are of the same order of magnitude, and the mirrors are selected to distort the images so that the images formed on the various sides of the sample have approximately the same size and width to length ratio. In this manner each point along the entrance slit of the emission monochromator is filled with light of the intensity substantially corresponding to illumination of the sample with light from all points along the length of the excitation monochromator's exit slit, with the result that a very substantial increase in the intensity of the output signal is achieved. With this arrangement the slit image is projected into the sample with ample free surface remaining around the sample thereby increasing access to the sample.

In accordance with another feature of an advantageous embodiment of the invention, optical wedge shaped elements are positioned adjacent the sample in the path of the light beams to and from the respective monochromators to condense and concentrate the excitation beam at the axial intersection of the respective beams and to pick up more emitted light to provide an additional improvement in the output intensity.

In accordance with a further feature of certain embodiments of the invention, the extreme rays between the images of the two apertures in the excitation monochromator illuminates a sample volume in the approximate shape of a right rectangular prism. The width of the beam passing through the sample is comparatively uniform and is maintained as small as practical, with the result that the intensity of the output signal is further increased.

The above, and other objectives, features and advantages of the present invention will be apparent from the following detailed description of certain preferred embodiments thereof which is to be read with reference to the accompanying drawings, wherein:

BRIEF DESCRIPTION OF THE DRAWINGS

FIG. 3 is a simplified schematic plan view of a fluorescence spectrophotometer in accordance with another illustrative embodiment of the invention.

FIG. 4 is an elevational view taken along line 4—4 of FIG. 3 showing a portion of the spectrophotometer illustrated in that Figure.

FIG. 5 is an elevational view taken along line 5—5 of FIG. 3 showing the spectrophotometer portion illustrated in FIG. 4.

FIG. 6 is a horizontal sectional view of a sample holder useful in connection with the invention.

DESCRIPTION OF CERTAIN PREFERRED EMBODIMENTS

Figure 1:
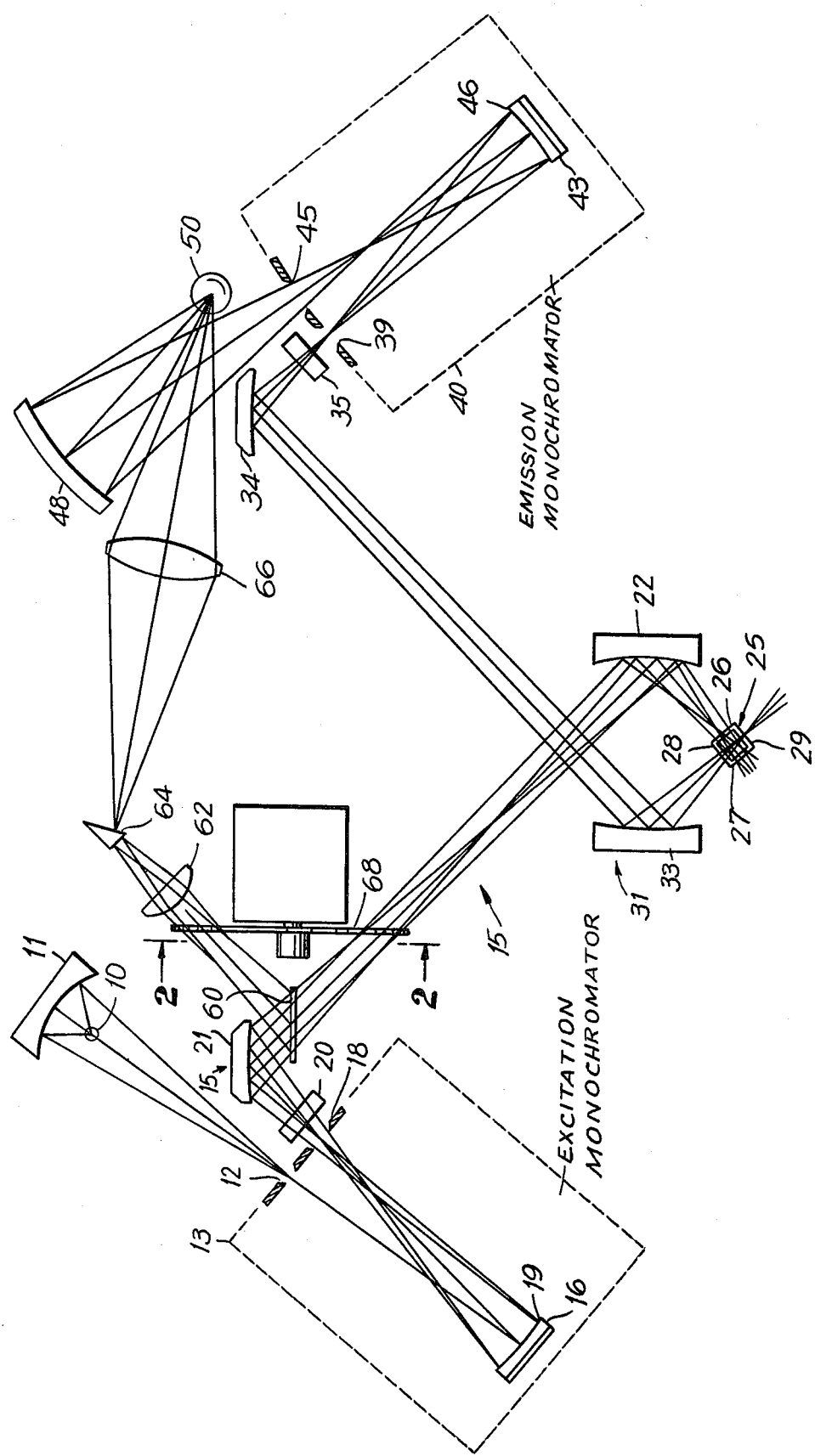
FIG. 1 is a simplified schematic plan view of a fluorescence spectrophotometer in accordance with one illustrative embodiment of the invention.

Referring to FIG. 1 of the drawings, there is shown a schematic representation of a fluorescence spectrophotometer having a xenon arc or other suitable source 10 of visible or invisible light. Light from the source 10 is collected by a concave mirror 11 and is focused onto the adjustable entrance slit 12 of an excitation monochromator 13. The aperture defined by the entrance slit is of rectangular configuration with its longitudinal axis extending parallel to the plane of the drawing. The monochromator 13 is of a conventional type and includes, in addition to the entrance slit 12, a concave diffraction grating 16 and an adjustable exit slit 18 which likewise defines an aperture having its longitudinal axis extending parallel to the plane of the drawing. The light entering the entrance slit 12 is reflected by the grating 16 to the exit slit 18. The periphery of the grating 16 forms a first limiting aperture 19, for purposes that will become more fully apparent hereinafter.

The light emerging from the excitation exit slit 18 is in the form of a monochromatic excitation beam. This monochromatic beam is received by a first optical system 15 which comprises a filter 20 and two concave parabolic mirrors 21 and 22. The mirrors 21 and 22 are preferably oriented at 45° angles with respect to the principal ray of the incident beam to direct the light toward a sample holder or cell 25. The sample cell 25 is of square configuration and includes opposed pairs of flat surfaces 26 and 27, and 28 and 29. The optical system 15 forms a real horizontal image 30 (FIG. 1A) of the aperture defined by the excitation exit slit 18 closely adjacent the surface 26 of the sample cell 25.

In addition to the excitation exit slit image the first optical system is effective to form an image 31 of the grating aperture 19. This latter image is located in close proximity with the surface 27 of the sample cell 25, that is, the surface opposite the surface 26 and the exit slit image 30. The longitudinal axis of each of the images 30 and 31 lies in a single plane parallel to the plane of the drawing.

The filter 20 removes light of undesired wavelengths from the excitation beam leaving the slit 18 and transmits the rest of the excitation beam to the first concave mirror 21 which is set at an angle of about 45° to the optical axis of the excitation beam. The beam is reflected to the mirror 22 which is positioned at right angles to mirror 21. Mirrors 21 and 22 form the excitation optical system 15 for the instrument and direct the excitation beam from the exit slit 18 to sample holder 25. The optical system is relatively simple, but its magnifications in the horizontal and vertical directions are such that the length of the exit slit image 30 is approximately equal to the length of the aperture image 31. The width of the exit slit image 30 is equal to the width of the aperture image 31 at an intermediate slit width between the widest and narrowest possible slit widths in the monochromator. At this intermediate slit width, the extreme rays between the images 30 and 31 illuminate a sample volume in the approximate shape of a right rectangular prism. The width of the beam passing through the sample is comparatively uniform and is maintained as small as practical, with the result that the intensity of the beam is substantially increased. Moreover the space around the sample holder is free of obstructions so that access to the sample holder is improved.

The excitation beam passing through sample 25 excites the sample and causes it to emit fluorescence of a wavelength different from that of the exciting light. This fluorescence is emitted in all directions. A portion of the emitted fluorescence is collected by a concave mirror 33 and is directed thereby to a second concave mirror 34 and then to a filter 35. The mirrors 33 and 34 form an emission optical system 31 which is identical with the excitation optical system 15. In a manner similar to that of the mirrors 21 and 22, the mirrors 33 and 34 are oriented at forty-five degree angles with respect to the principal rays of the emission beam collected from the sample 25. These mirrors have the same differential focal properties in the horizontal and vertical directions and form distorted images of the illuminated part of the sample at the entrance slit 39 and grating 46 of an emission monochromator 40.

The entrance slit 39 is of rectangular configuration and has its longitudinal axis extending in a direction parallel to the plane of the drawing. The monochromator 40 is similar to the excitation monochromator 13 and, in addition to the entrance slit 39, includes a concave diffraction grating 43 and an exit slit 45 parallel to the entrance slit. The fluorescence enters the entrance slit 39, and is reflected by grating 43 toward exit slit 45. The periphery of the grating 43 defines a limiting aperture 46.

The light emerging from exit slit 45 comprises a selected, highly monochromatic portion of the luminescent emission from sample 25. The emerging light is received by a concave mirror 48 which focuses the light beam on a photoelectric detector 50 which is of conventional construction and preferably is of a type which exhibits high sensitivity at the particular wavelengths of interest. The detector 50 produces an output signal proportional to the intensity of the light from the exit slit 45.

Figure 1A:
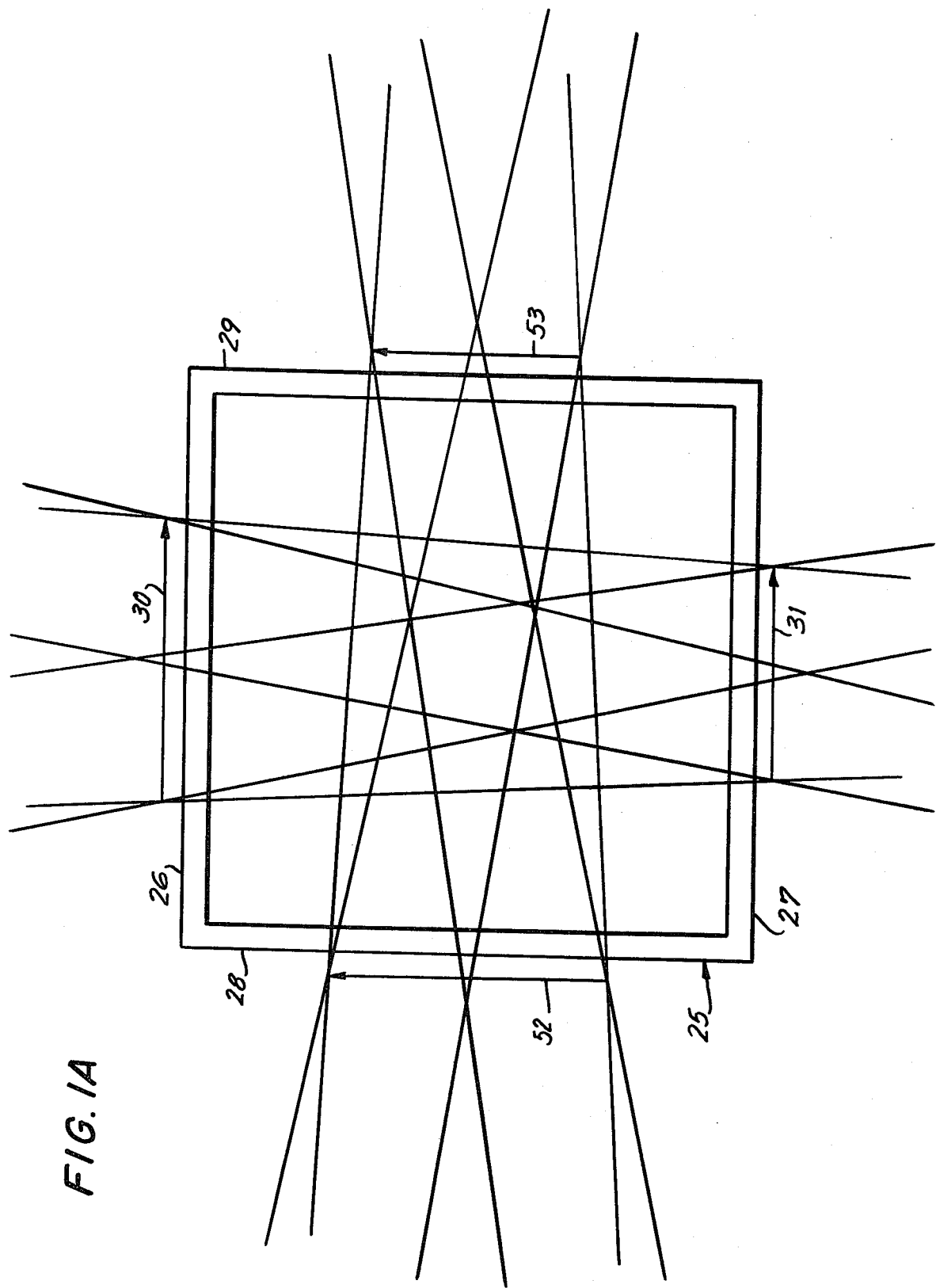
FIG. 1A is an enlarged schematic plan view of the light paths adjacent the sample holder of the spectrophotometer shown in FIG. 1.

The mirrors 33, 34 in the optical system for the emission monochromator 40 form an optical image 52 of the aperture defined by the emission entrance slit 39. This image is located in close juxtaposition with the surface 28 of the sample cell 25 (FIG. 1A). Similarly, a reduced optical image 53 of the grating aperture 46 is formed adjacent the opposite surface 29 of the sample cell. The extreme rays between the images 52 and 53 outline a sample volume in the approximate shape of a right rectangular prism, and the width of the beam passing through the sample is comparatively uniform and is as small as practical.

The principal rays of the beam from the excitation monochromator 13 and the beam approaching the emission monochromator 40 intersect at the sample cell 25. The longitudinal axis of each of the aperture images 30, 31, 52 and 53 lies in a plane defined by these principal rays. The image 30 of the exit slit 18 is parallel to the path of the emission beam, and the image 52 of the entrance slit 39 is parallel to the path of the excitation beam. The arrangement is such that each point along the entrance slit 39 is filled with light of an intensity corresponding to the irradiation of the sample with light from the entire length of the exit slit 18.

In the excitation and emission optical systems the use of mirrors rather than lenses for focusing reduces the amount of chromatic aberration in the system as compared to an optical system relying primarily on lenses for focusing. Preferably the mirrors of the optical systems have anamorphic properties that distort the slit and grating images in such a way that both images have about the same length to width ratio. The aperture image produced at the sample cell is a reduced and distorted image of the grating aperture.

Figure 2:
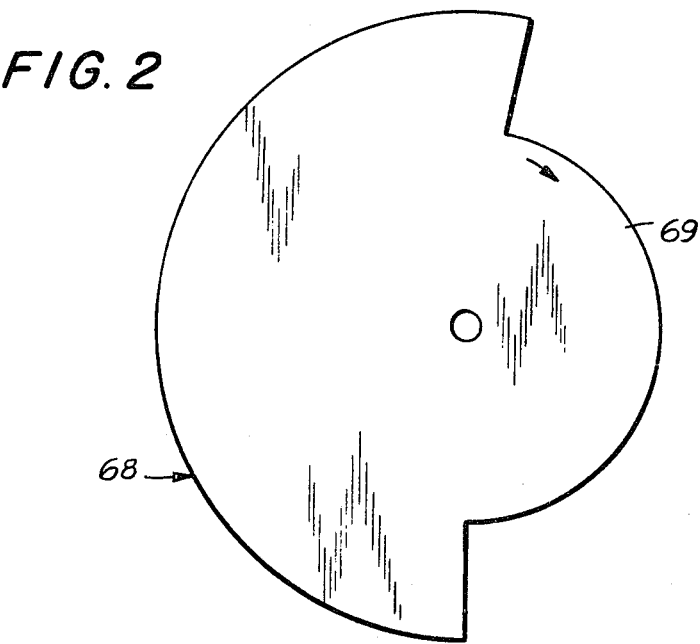
FIG. 2 is an elevational view taken along line 2—2 of FIG. 1 showing a light chopper used in conjunction with the spectrophotometer of FIG. 1.

The spectrophotometer of FIG. 1 also includes a beam splitter 60 which receives the monochromator excitation beam reflected by mirror 21. The beam splitter illustratively is in the form of a flat quartz plate or a partially reflecting mirror. A known fraction of the received light is reflected by the beam splitter and is directed through a plano-convex lens 62 to a hollow prism 64 containing rhodamine B solution or other so-called quantum detecting liquid that absorbs light of all wavelengths incident on it and remits a fraction of quanta in this light at a fixed wavelength. A double convex lens 66 focuses the emitted light on the photoelectric cell 50. This fraction is used as a reference beam and is periodically interrupted by a continuously rotating chopper 68 between the splitter 60 and the lens 62. The chopper is oriented, as seen in FIG. 1, to also periodically interrupt the monochromatic excitation beam between the splitter 60 and the mirror 22. The chopper is provided with an arcuate cutout 69 (FIG. 2) which simultaneously allows the monochromatic beam to pass to the sample and blocks the reference beam to the photocell and to thereafter block the monochromatic beam and pass the reference beam to the photocell.

The photocell 50 is thus alternately illuminated by monochromatic light from the luminescent sample in the cell 25 and by reference light from the quantum counter 64. The light detected by the photocell is alternately representative of the unknown luminescent intensity from the sample and the intensity of the reference beam. By using conventional electrical circuitry the output signals from the photocell may be translated into a net output signal corresponding to the ratio of the net sample signal to the net reference signal.

Figure 7:
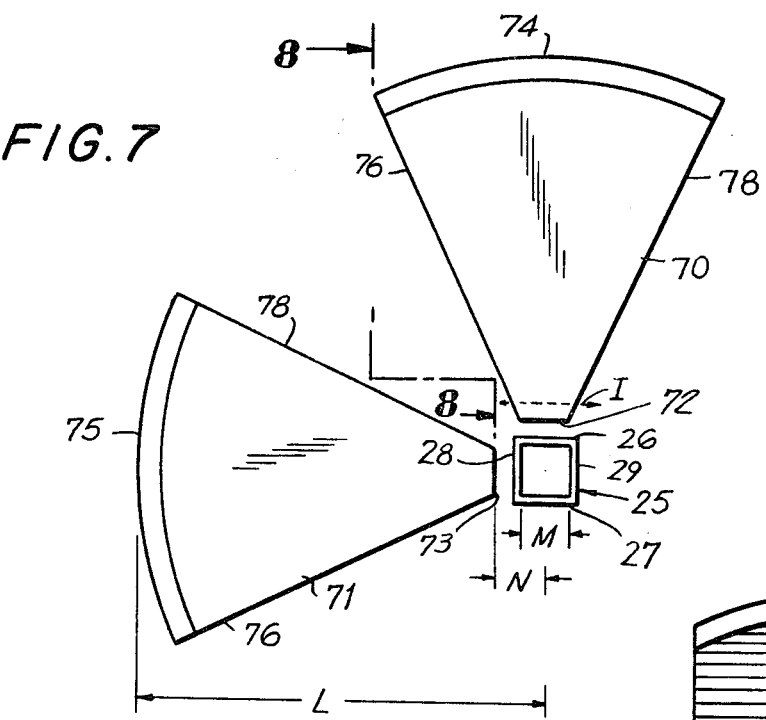
FIG. 7 is a plan view of optical wedges and associated components useful in connection with the invention shown in FIG. 1.
Figure 8:
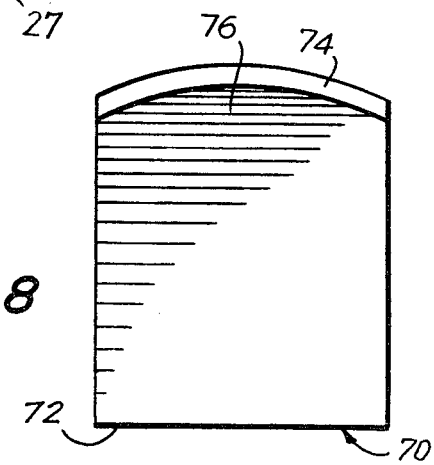
FIG. 8 is an elevational view taken along line 8—8 of FIG. 7.

The light intensity to which the sample in the sample cell 25 is subjected can be further increased in the embodiment of FIG. 1 by the use of two optical elements 70 and 71 (FIG. 7). The elements 70 and 71 are shaped like wedges taken from a sphere, having flat or beveled inner ends 72 and 73, respectively, and spherical outer surfaces 74 and 75, respectively. The center of curvature of the spherical surfaces 74 and 75 is located near the axial center of their bevels. The wedges are positioned adjacent the sample holder 25 near the faces 26 and 28, respectively, in order to be in the optical path of the monochromatic excitation beam and the fluorescent emission beam produced by the sample.

In one embodiment of the invention, the apparatus uses a wedge whose overall length from the maximum radius thereof to its inner beveled surface is thirteen millimeters, with the inner beveled surface spaced two millimeters from the center of the sample cell 25, so that the overall distance from the maximum radius to the center of the sample is fifteen millimeters. These wedges have flat converging side surfaces 76 and 78 as seen in FIG. 7, and serve to concentrate more of the excitation light on a small sample at the axial intersection of the optical axes of the light beams passing through the wedges and the sample, and to pick up more emitted light from the sample. Among their other advantages, the wedges are substantially cheaper and easier to manufacture than the two-dimensionally tapered systems use in cone or pyramid optics, for example.

In use, an image of the exit slit 18 of the monochromator 13 is projected into the wedge 70 to form an illuminated band, illustratively six millimeters long, and represented by the double headed arrow I in FIG. 7. The light rays which otherwise would go to the ends of the image are intercepted by the polished wedge faces 76 and 78 and are reflected through the bevel, as is the case in cone optical systems. With the geometry shown and specified above, the wedge will illuminate a length of two millimeters at the bevel instead of the original 6 millimeters of the slit image. The resultant illumination band expands to about three millimeters at the axial intersection of the axes of the wedges 70 and 71. Thus, a three millimeter target at this intersection receives all of the light instead of only the half of the light that it would have received if the wedge were absent. The light distribution on the target is such that the central two millimeter portion receives more than two thirds of the light and possibly as much as three quarters.

For example, in a sample which is two millimeters long in the plane of the drawing (e.g., a rod two millimeters in diameter standing perpendicular to the plane of the paper), one third of the excitation light is intercepted without the use of the wedge 70, while as much as three quarters of the available light is intercepted when the wedge is used. This represents a light increase of 2.25 times that which is available without the wedge. Similarly, the wedge 71 picks up 2.25 times more light from the rod sample than would be collected without it.

For a small sample the improvement in light intensity is cumulative for the excitation and emission beams and amounts to almost a five times signal increase projected to the photocell.

The spherical surfaces 74 and 75 on the wedges 70 and 71 contribute still another increase in signal by reducing the original slit image to a smaller image than the 6 millimeters assumed above. With the slit image near the center of curvature, the reduction factor equals the index of refraction, or approximately 1.5 if a silica material is used to form the wedge. In the plane of the drawing, this makes a further intensity increase that is again cumulative. In the plane perpendicular to the drawing the increase is not cumulative because it is assumed that the sample rod is taller than the part of it that is to be illuminated. Thus, the effect of the surfaces is to increase the signal by 3.37 times, which is 1.5 to the third power. As this is separate from the previously described effect of the wedges, the combined signal increase is 5 times 3.37 or almost 17 times. Because of reflection losses, with internally reflecting wedges, the actual signal increase is about 13.5; with aluminized wedges it is about 12.7.

If the same beam condensing wedges are used with a set of sample optics in a spectrometer that forms slit images oriented perpendicular to the plane of the paper, the effect of the wedges is to increase intensity on the sample, but not to recover any light that would otherwise be lost, with a resultant gain of 3. Simultaneously, the effect of the spherical wedge surface is to increase the signal by an additional factor of 1.5, for a combined increase of about 4.5. Allow for reflection losses with aluminized wedges this becomes 3.3 times, which may be compared with 12.7 times obtained under the conditions discussed above. The 3.8 fold difference between these factors arises primarily from the light that is lost past the edges of the sample when the split images are not in the plane of the optic axis.

The embodiment of the invention illustrated in FIG. 3 includes a light source 80 and a source condensing mirror 81 which are similar to those described previously. An excitation monochromator 82 receives light from the source 80 through a vertical entrance slit 83, whence it passes to a collimating mirror 84 that converts its divergent beam into an essentially parallel beam for illuminating a grating 85. Part of the dispersed light from the grating falls on a telescope mirror 86 which focuses a spectrum at a vertical exit slit 87. The slit 87 selects a portion of the dispersed spectrum and passes it as a nearly monochromatic beam to an associated optical system including mirrors 88, 89, 90, 91 and 92.

This optical system serves several important functions. First, it forms a reduced image of the exit slit 87 adjacent the facing surface of a sample holder 107 and a reduced image of the limiting aperture from the grating 85 adjacent the opposite surface. Second, it is composed solely of reflective optical elements causing the images to be completely free from chromatic aberration. Third, it rotates the beam of light ninety degrees around the direction of propagation with the result that the length of the slit image that is formed near the sample lies in the horizontal plane instead of perpendicular thereto. Fourth, it distorts the slit and grating images in the sense that the slit image is shorter and wider than the actual slit and the grating image longer and narrower than the actual grating. Fifth, it sets the amount of reduction and distortion at those values that make the slit and grating images approximately the same size and shape. In the same way that was discussed above, the light paths between the slit and grating images are all included within a small right rectangular prism.

The mirror 88 receives the monochromatic excitation beam from the exit slit 87 and directs the beam to the mirror 89. In an illustrative embodiment the mirror 88 is located 48 mm from the exit slit 87 and is of toroidal configuration with radii of 116.5 in the horizontal direction and 82.0 mm in the vertical direction. It forms a highly astigmatic virtual image of the slit 87 back inside the monochromator 82 and a highly astigmatic real image of the grating between itself and the mirror 89. This latter mirror is flat and is inclined upward forty-five degrees to direct the reflected beam vertically upward.

From the mirror 89 the excitation beam proceeds to a cylindrical mirror 90 and then to a flat mirror 91. The mirror 90 illustratively is located 26 mm above the mirror 89 and again is inclined at 45° to the incident ray, but in a plane ninety degrees away from the plane of the mirror 89. The mirror 91 also is inclined at 45° to the incident ray but in still a third plane. As best shown in FIGS. 4 and 5, one action of this group of mirrors is first to reflect the light upward from the mirror 89, then horizontally from the mirror 90, and then backward from the mirror 91 in the direction from whence it came but offset from the original line 26 mm upwardly and 20.7 mm horizontally. In these reflections the vertical slit and grating images are rotated to form horizontal images.

The mirror 88 (FIG. 3) has concave radii in both planes, such that when used at a 45° angle of incidence it has a shorter focal length, or stronger positive focusing power, in the plane of the paper than in the plane perpendicular to the paper. Thus, the virtual exit slit image that it forms in the vertical plane is less magnified than and nearer to the exit slit 87 than the vertical slit image in the horizontal plane. Conversely, because the grating image is real, the grating image in the vertical plane is more magnified than and further from the mirror 88 than the grating image in the horizontal plane.

The cylindrical mirror 90 illustratively has a convex radius of 285 mm in the plane of incidence: i.e., in a direction perpendicular to the length of the exit slit image. The mirror 90 exhibits more negative focusing power in this direction than in the direction of the slit length. This amount of negative power at this location in the optical system serves to correct the astigmatism introduced into both the slit image and the grating image by the torroidal mirror 88, with the result that the slit and grating images are substantially stigmatic. The distortion introduced into the two images by these two mirrors, however, is not canceled. To achieve these two results the mirror 88, which is nearer the slit, must form virtual slit images and real grating aperture images and must have more positive focusing power in the direction of the slit width than at right angles thereto. The mirror 90, on the other hand, must have less positive focusing power (or more negative focusing power) in the direction of the slit width than in the perpendicular direction. In the plane perpendicular to the slit length, the negative cylindrical power of the mirror 90 forms reduced virtual images of the slit and grating images already formed by the mirror 88. Within the accuracy necessary for the proper functioning of the system, the image locations coincide with the locations of the corresponding images that are formed in the other plane by the mirror 88.

The mirror 91 reflects the excitation beam to a curved mirror 92. This latter mirror has an ellipsoidal form with major and minor image distances which illustratively are 132.7 and 57.3 mm, respectively. The mirror 92 is located 51.0 mm from the center of the sample within the cell 107, and it forms an accurate but distorted grating image just behind the sample and a less accurate but also distorted exit slit image just in front of the sample. The mirror 92 reduces both of these images to approximately the same size.

Located in close juxtaposition with the rear surface of the sample holder 107 is a concave meniscus mirror 93. The mirror 93 serves as a retro mirror and has a radius of curvature suitable to form a second image of the excitation exit slit adjacent the front surface of the sample holder, thus passing the excitation light twice through the same volume of sample.

The excitation beam passing through the sample excites the sample and causes it to emit fluorescence of a wavelength different from that of the exciting light, as in the previous embodiment. This fluorescence is emitted in all directions. A portion of the emitted fluorescence is collected by a second optical system associated with the remaining opposed surfaces of the sample cell 107 to form an emission beam. The second optical system includes mirrors 97, 98, 99 and 100 which perform the corresponding functions of imagery, rotation, distortion and reduction in the emission beam that the group of mirrors 88 through 92 serve in the excitation beam. The mirrors 97 and 100 are aspherically concave and may be identical to their counterpart mirrors 92 and 88, respectively, with their distances from the slit and sample and from each other the same as the corresponding distances in the excitation beam. In the illustrative embodiment of FIG. 3 there is no counterpart in the emission system for the flat mirror 91 because mechanical convenience does not require it, and indeed in other embodiments the mirror 91 may not be needed depending upon the physical location of the various system components. Also, the negative cylindrical power in the excitation system mirror 90 appears in the emission system in the mirror 99, and because the mirror 99 is tilted in a different direction from the mirror 90 its convex radius is 142.6 mm, exactly half that of mirror 90. None of these differences significantly affects the performance of the optical systems. Identical stigmatic but distorted slit and grating images are formed adjacent the opposed pairs of surfaces of the sample holder 107.

A concave retro mirror 120 is located in position to reflect additional emitted light through the sample to the mirror 97. Contrary to the retro mirror 93 in the excitation system, the mirror 120 is remote from the sample holder 107 and has its center of curvature close to the center of the sample. The light path still traverses essentially the same part of the sample twice, but the imagery is inverted between the two. In each system the effect of the second traversal through the sample is to almost double the intensity of fluorescent light collected. In the excitation system, the increase comes from doubling the excitation power density in the sample; in the emission system the increase comes from doubling the effective thickness of illuminated sample that is observed.

An advantage of the concave retro mirrors 93 and 120 over, say, flat mirrors is that the imaging properties of the concave mirrors preclude the possibility of divergent light rays that might otherwise strike the walls of the sample cell 107 on the second pass through the cell. This is a particularly important feature in measuring weak samples whose fluorescence might otherwise be concealed by scattered light from the walls.

Following the group of mirrors 97 through 100, the emission beam is directed through the vertical entrance slit 102 of an emission monochromator 101. The emission monochromator 101 may be similar to the excitation monochromator 82 and includes a collimator 103 which illuminates a diffraction grating 104 with an essentially parallel beam of light. Part of the diffracted beam is focused by a telescope mirror 105 on and through a vertical exit slit 106. Monochromatic light isolated thereby reaches a photomultiplier detection system 155 in a manner similar to that described heretofore.

In the embodiment of FIG. 3 the sample cell 107 is supported adjacent the periphery of a rotatable table 111. The table 111 is of circular configuration and includes three additional sample cells 108, 109 and 110 which may contain different fluorescent materials. The various sample cells are spaced at ninety degree intervals on the table 111 such that the sample being evaluated may be readily changed merely by pivoting the table through a corresponding angle. Concave meniscus mirrors 94, 95 and 96, each similar to the mirror 93, are located adjacent the inwardly facing surfaces of the cells 108, 109 and 110, respectively, for directing the excitation beam back for a second pass during the evaluation of the corresponding samples.

Another advantageous form of turret and retro mirror arrangement is illustrated in FIG. 6. Four sample cells 156, 157, 158 and 159 are respectively mounted adjacent the four corners of a square table 160 which is supported for pivotal movement about a vertical axis 161. Each of the cells 156, 157, 158 and 159 has one corner facing the axis 110, instead of a flat surface facing the axis as shown in FIG. 3. Behind the adjacent inner surfaces of each cell are concave reflectors 162 and 163. In the FIG. 6 embodiment each of the reflectors 162 and 163 is in the form of a two-sided first surface mirror, although in other arrangements the reflectors may be the same as the mirrors 93, 94, 95 and 96 of FIG. 3. The reflectors 162 and 163 serve as retro mirrors for the excitation and emission optical systems, respectively, in a manner similar to that described above.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. Apparatus for measuring radiation from a sample, the apparatus comprising, in combination:
   a source of radiation;
   excitation monochromator means for isolating an excitation beam of monochromatic radiation from said source, the excitation monochromator means having means for receiving radiation from said source, an excitation exit slit, and means for directing a part of the received radiation through said excitation exit slit;
   first means cooperating with the excitation monochromator means for directing the excitation beam to said sample and for forming an image of the excitation exit slit;

emission monochromator means for isolating radiation from said sample, the emission monochromator means having an emission entrance slit for receiving an emission beam of radiation from said sample, an emission exit slit, and means for directing monochromatic radiation from the emission beam through said emission exit slit;

second means cooperating with the emission monochromator means for directing the emission beam to the emission entrance slit and for forming an image of said emission entrance slit;

said excitation beam and said emission beam having axial rays which intersect at said sample, and each of said images having a longitudinal axis which lies in the plane defined by said axial rays; and radiation detecting means for receiving the monochromatic radiation from the exit slit of the emission monochromator means;

said first and second means each comprising a plurality of optical elements including a pair of aspherically concave mirrors angularly related to each other.

2. Apparatus as defined in claim 1, in which one of said mirrors in each pair is adjacent an associated slit in its associated monochromator means and the other mirror is adjacent the sample; said one mirror having a longer focal length in the direction of the slit length than the focal length in the direction perpendicular to the slit length, and said other mirror having a shorter focal length in the direction of the slit image length than the focal length in the direction perpendicular thereto.

3. Apparatus as defined in claim 2 wherein said mirror adjacent the sample is ellipsoidal.

4. Apparatus for measuring radiation from a sample, the apparatus comprising, in combination:
a source of radiation;
excitation monochromator means for isolating an excitation beam of monochromatic radiation from said source, the excitation monochromator means having an excitation exit slit for said excitation beam;
first optical means cooperating with the excitation monochromator means for directing the excitation beam to said sample and for forming a distorted image of the excitation exit slit adjacent said sample, said exit slit image having a length to width ratio smaller than the length to width ratio of the excitation exit slit;
emission monochromator means for isolating radiation from said sample, the emission monochromator means having an emission entrance slit for receiving an emission beam of radiation from said sample;
second optical means cooperating with the emission monochromator means for directing the emission beam to the emission entrance slit and for forming a distorted image of said emission entrance slit adjacent said sample, said entrance slit image having a length to width ratio smaller than the length to width ratio of said emission entrance slit;
said excitation beam and said emission beam having axial rays which intersect at said sample; and
radiation detecting means for receiving the monochromatic radiation from the emission monochromator means;

said first and second optical means each comprising an optical system including a pair of concave mirrors successively disposed along the optical axis of the corresponding beam, the mirrors in each pair being angularly related to each other and selected to form the associated distorted image with its longitudinal axis lying in a plane defined by said intersecting axial rays.

5. Apparatus as defined in claim 4, in which one of said mirrors in each of said pairs is adjacent an associated slit in its associated means monochromator and the other mirror is adjacent the sample, said one mirror having a longer focal length in the direction of the slit length than the focal length in the direction perpendicular to the slit length, and said other mirror having a shorter focal length in the direction of the slit image length than the focal length in the direction perpendicular thereto.

6. Apparatus as defined in claim 4 wherein the exit slit of said excitation monochromator means and the entrance slit of said emission monochromator means are horizontal.

7. Apparatus as defined in claim 4 wherein the exit slit of said excitation monochromator means and the entrance slit of said emission monochromator means are vertical, said first and second optical means each including means for horizontally orienting the corresponding slit image.

8. Apparatus as defined in claim 4 wherein the first of said concave mirrors along the optical axis of said excitation beam forms an astigmatic image of the exit slit of said excitation monochromator means with more magnification in the direction of the exit slit width than in the direction of the exit slit length, and the second concave mirror along the optical axis of said excitation beam combines the two astigmatic foci of the exit slit image into a distorted stigmatic image with a smaller length to width ratio than the length to width ratio of the exit slit.

9. Apparatus as defined in claim 8 wherein said pair of mirrors along the optical axis of the emission beam are optically identical to the pair of mirrors along the optical axis of the excitation beam.

10. Apparatus for measuring radiation from a sample having pairs of opposed surfaces, the apparatus comprising, in combination:
a source of radiation;
excitation monochromator means for isolating an excitation beam of monochromatic radiation from said source, the excitation monochromator means having an excitation entrance slit for receiving radiation from said source, an excitation exit slit, and means for directing the excitation beam through said excitation exit slit;
a first optical system cooperating with the excitation monochromator means for forming a distorted image of said excitation exit slit in close juxtaposition with a first surface of said sample, the excitation exit slit image having a length to width ratio smaller than the length to width ratio of the excitation exit slit;
emission monochromator means for isolating radiation from said sample, the emission monochromator means having an emission entrance slit for receiving an emission beam of radiation from said sample, an emission exit slit, and means for directing monochromatic radiation from the emission beam through said emission exit slit;

a second optical system cooperating with the emission monochromator means for forming a distorted image of said emission entrance slit in close juxtaposition with a second surface of said sample, the emission entrance slit image having a length to width ratio smaller than the length to width ratio of said emission entrance slit;

said excitation beam and said emission beam having axial rays which intersect at said sample, and each of said images having a longitudinal axis which lies in the plane defined by said intersecting axial rays; and radiation detecting means for receiving the monochromatic radiation from the exit slit of the emission monochromator means;

said first and second optical systems each including a pair of cooperating aspherically concave mirrors angularly related to each other for forming the associated distorted image.

11. Apparatus as defined in claim 10, wherein said excitation exit slit and said emission entrance slit each have their longitudinal axis oriented perpendicularly to said plane, and in which each of said optical systems includes a pair of mirrors oriented at 45° angles with respect to the axial ray of the radiation incident thereto to position the longitudinal axes of said images in said plane.

12. Apparatus for measuring radiation from a sample, the apparatus comprising, in combination:

a source of radiation;

excitation monochromator means for isolating an excitation beam of monochromatic radiation from said source, the excitation monochromator means receiving radiation from said source and having an excitation exit slit defining a first limiting aperture, means for directing the excitation beam through said excitation exit slit, and means defining a second limiting aperture for the excitation beam;

first optical means cooperating with the excitation monochromator means for directing the excitation beam to said sample and for forming first and second distorted images of the respective first and second limiting apertures;

emission monochromator means for isolating radiation from said sample, the emission monochromator means having an emission entrance slit defining a third limiting aperture for receiving an emission beam of radiation from said sample, and means defining a fourth limiting aperture for the emission beam;

second optical means cooperating with the emission monochromator means for directing the emission beam to the emission entrance slit and for forming third and fourth distorted images of the respective third and fourth limiting apertures;

said excitation beam and said emission beam intersecting at said sample; and radiation detecting means for receiving the monochromatic radiation from the exit slit of the emission monochromator means;

said first and second optical means each including at least one aspherically concave mirror for forming the distorted images in the corresponding beam, the distorted images in each of said beams having approximately the same length and lying with their longitudinal axes in the plane defined by said intersecting axial rays.

13. Apparatus for measuring radiation from a sample having pairs of opposed surfaces, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit defining a first limiting aperture, and means for directing the excitation beam through said excitation exit slit, the excitation monochromator means including means defining a second limiting aperture for the excitation beam;

first optical means cooperating with the excitation monochromator means for forming a first distorted image of said first limiting aperture adjacent a first surface of said sample and a second distorted image of said second limiting aperture adjacent a second surface of said sample, said first distorted image having a smaller length to width ratio than that of said first limiting aperture;

emission monochromator means for isolating radiation from said sample, the emission monochromator means having an emission entrance slit defining a third limiting aperture for receiving an emission beam of radiation from said sample, an emission exit slit, and means for directing monochromatic radiation from the emission beam through said emission exit slit, the emission monochromator means including means for defining a fourth limiting aperture for the emission beam;

second optical means cooperating with the emission monochromator means for forming a third distorted image of said third limiting aperture adjacent a third surface of said sample and a fourth distorted image of said fourth limiting aperture adjacent a fourth surface of said sample, said third distorted image having a smaller length to width ratio than that of said third limiting aperture;

said excitation beam and said emission beam having axial rays which intersect at said sample, and each of said distorted images having a longitudinal axis which lies in the plane defined by said axial rays; and radiation detecting means for receiving the monochromatic radiation from the exit slit of the emission monochromator means;

said first and second optical means each including a pair of cooperating concave mirrors successively disposed along the optical axis of the corresponding beam, said concave mirrors being angularly related to each other for forming the distorted images in said corresponding beam.

14. Apparatus for measuring radiation from a sample having pairs of opposed surfaces, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit defining a first limiting aperture, and means for directing the excitation beam through said excitation exit slit, the excitation monochromator means including means defining a second limiting aperture for the excitation beam;

a first optical system cooperating with the excitation monochromator means for forming a first distorted image of said first limiting aperture adjacent a first surface of said sample and a second distorted image of said second limiting aperture adjacent a second surface of said sample, said first distorted image having a smaller length to width ratio than that of said first limiting aperture;

emission monochromator means for isolating radiation from said sample, the emission monochromator means having an emission entrance slit defining a third limiting aperture for receiving an emission beam of radiation from said sample, an emission exit slit, and means for directing monochromatic radiation from the emission beam through said emission beam through said emission exit slit, the emission monochromator means including means defining a fourth limiting aperture for the emission beam;

a second optical system cooperating with the emission monochromator means for forming a third distorted image of said third limiting aperture adjacent a third surface of said sample and a fourth distorted image of said fourth limiting aperture adjacent a fourth surface of said sample, said third distorted image having a smaller length to width ratio than that of said third limiting aperture;

said excitation beam and said emission beam having axial rays which intersect at said sample, and each of said distorted images having a longitudinal axis which lies in the plane defined by said axial rays;

the longitudinal axis of said first distorted image extending in a direction parallel to the principal ray of the emission beam, and the longitudinal axis of said third distorted image extending in a direction parallel to the principal ray of the excitation beam; and radiation detecting means for receiving the monochromatic radiation from the exit slit of the emission monochromator means;

said first and second optical systems each including a pair of cooperating concave mirrors angularly related to each other for forming said distorted images in said plane.

15. Apparatus as defined in claim 14, in which the longitudinal axis of said second distorted image extends in a direction parallel to the principal ray of the emission beam, and the longitudinal axis of said fourth distorted image extends in a direction parallel to the principal ray of the excitation beam.

16. Apparatus as defined in claim 15, wherein said distorted images each have approximately the same length to width ratios.

17. Apparatus for measuring radiation from a sample having pairs of opposed surfaces, the apparatus comprising, in combination:

a source of radiation;

excitation monochromator means for isolating an excitation beam of monochromatic radiation from said source, the excitation monochromator means having an excitation entrance slit for receiving radiation from said source, an excitation exit slit defining a first limiting aperture, and means for directing the excitation beam through said excitation exit slit, the excitation monochromator means including means defining a second limiting aperture for the excitation beam;

a first optical system for directing the excitation beam toward said sample, said first optical system forming a first anamorphic distorted image of said first limiting aperture adjacent a first surface of said sample and forming a second anamorphic distorted image of said second limiting aperture adjacent a second surface of said sample;

emission monochromator means for isolating radiation from said sample, the emission monochromator means having an emission entrance slit defining a third limiting aperture for receiving an emission beam of radiation from said sample, an emission exit slit, and means for directing monochromatic radiation from the emission beam through said emission exit slit, the emission monochromator means including means defining a fourth limiting aperture for the emission beam;

a second optical system for receiving the emission beam from said sample and directing the same to the entrance slit of the emission monochromator means, the second optical system forming a third anamorphic distorted image of said third limiting aperture adjacent a third surface of said sample and forming a fourth anamorphic distorted image of said fourth limiting aperture adjacent a fourth surface of said sample;

said excitation beam and said emission beam having axial rays which intersect at the sample, and each of said images having a longitudinal axis which lies in the plane defined by said axial rays; and radiation detecting means for receiving the monochromatic radiation from the exit slit of the emission monochromator means;

said first and second optical systems each including a pair of cooperating concave mirrors angularly related to each other for forming said anamorphic distorted images in said plane.

18. Apparatus as defined in claim 17, in which the excitation beam has extreme rays between said first and second distorted images which illuminate a volume of said sample in the approximate shape of a right rectangular prism, and the emission beam has extreme rays between said third and fourth distorted images which are illuminated by radiation from a volume of said sample in the approximate shape of a right rectangular prism.

19. Apparatus for measuring radiation from a sample, the apparatus comprising, in combination:

a source of radiation;

excitation monochromator means for isolating an excitation beam of monochromatic radiation from said source, the excitation monochromator means having an excitation entrance aperture for receiving radiation from said source, an excitation exit slit, and means including a second aperture for directing a part of the received radiation through said excitation exit slit to form said excitation beam;

first mirror means cooperating with the excitation monochromator means for directing the excitation beam to said sample and for forming a distorted substantially stigmatic image of the excitation exit slit;

emission monochromator means for isolating radiation from said sample, the emission monochromator means having an emission entrance slit for receiving an emission beam of radiation from said sample, an emission exit slit, and means for directing monochromatic radiation from the emission beam through said emission exit slit;

second mirror means cooperating with the emission monochromator means for directing the emission beam to the emission entrance slit and for forming a distorted substantially stigmatic image of said emission entrance slit;

said excitation beam and said emission beam having axial rays which intersect at said sample, and each of said images having a longitudinal axis which lies in the plane defined by said axial rays; and radiation detecting means for receiving the monochromatic radiation from the exit slit of the emission monochromator means.

* * * * *